United States Patent [19]

Hanz

[11] Patent Number: 4,688,780

[45] Date of Patent: Aug. 25, 1987

[54] PATIENT SUPPORT

[75] Inventor: George Hanz, Bloomingdale, Ill.

[73] Assignee: Siemens Gammasonics, Inc., Des Plaines, Ill.

[21] Appl. No.: 846,663

[22] Filed: Mar. 31, 1986

[51] Int. Cl.⁴ .............................................. A61G 13/00

[52] U.S. Cl. .................................................... 269/328

[58] Field of Search ................ 269/328, 322; 378/208, 378/209; 5/432, 433, 434, 435, 440; 297/460, 396

[56] References Cited

U.S. PATENT DOCUMENTS

| | | | |
|---|---|---|---|
| 2,133,223 | 10/1938 | Brightman et al. | 5/433 |
| 3,138,404 | 6/1964 | Newton | 297/460 |
| 3,449,570 | 6/1969 | Kok | 378/209 |
| 3,669,499 | 6/1972 | Semplonius et al. | 297/460 |
| 3,716,270 | 2/1973 | Frazier | 297/460 |
| 3,756,656 | 9/1973 | Weick | 297/460 |
| 4,300,249 | 11/1981 | Taylor | 297/460 |
| 4,555,139 | 11/1985 | Leib | 297/460 |
| 4,556,254 | 12/1985 | Roberts | 297/460 |
| 4,572,578 | 2/1986 | Perkins | 297/460 |

OTHER PUBLICATIONS

"Benchmark of Quality CT Somatom DR", published by Siemens AG, Order No. A19100-M2112-A141-0-1-7600.

*Primary Examiner*—Robert C. Watson
*Attorney, Agent, or Firm*—Mark H. Jay

[57] ABSTRACT

A patient support for scintillation camera imaging applications is formed as a unitary element having a generally constant wall thickness. The element has shoulder, neck and head sections shaped to receive a patient's shoulders neck, and head respectively, and at least two elongated and indented stiffening sections extending between the shoulder section and the neck section. Advantageously, each stiffening section has a bottom wall extending parallel to the surrounding unindented wall and oblique side walls, with gradual transitions between adjacent walls. In a preferred embodiment the unitary element is tiltably interlocked with a patient pallet by means of two offset projecting tabs inserted in mating pallet holes. The tilt angle may be controlled by inserting a wedge between the element and the pallet.

16 Claims, 7 Drawing Figures

PATIENT SUPPORT

BACKGROUND OF THE INVENTION

The invention relates to a support for properly positioning a patient during medical treatment and diagnosis. In particular, it relates to a support for positioning the head and upper part of a patient's body during a diagnostic imaging process.

There is known a positioning aid assembly composed of a head holder and a thorax cushion covered with a liner and a pad on top of the liner. Holder, cushion and pad are made from different resins, and the liner consists of a laminated piece of wood. The holder is tiltably connected to the liner by means of a metallic subassembly shaped like a cylinder and provided with an adjusting lever. Such a support has a relatively complicated and heavy structure which cannot be easily installed or removed, and allows only limited position changes. In addition, the different materials ąnd shapes used for the individual parts cause the imaging radiation to be greatly attenuated in locally varying degrees.

It is an object of the present invention to provide a support for the upper portion of a patient's body, which is simple and light and can easily be manufactured and handled.

It is another object to provide such a support which absorbs imaging radiation only slightly and uniformly.

It is a further object to provide such a support which is resilient such that its form adapts to different body shapes and which also has the necessary rigidity for carrying the body weight.

It is still a further object to provide such a patient support which allows a controlled elevation of the upper portion of the patient's body.

Yet another object is to improve on known devices of this type.

SUMMARY OF THE INVENTION

To achieve these and other objects, there is provided, in accordance with one aspect of the invention, a patient support having an unitary element of a generally constant wall thickness. The element has shoulder, neck, and head sections shaped to receive a patient's shoulders, neck and head respectively, and at least two elongated and indented stiffening sections extending between the shoulder section and the neck section.

According to another aspect of the invention, the shoulder section of the patient support has—at its end which is remote from the neck section—at least two offset projecting tabs, each being insertable in a mating hole of a pallet. With this simple interlock mechanism, the tray may easily be inserted and removed from a patient table.

In accordance with still another aspect of the invention, the patient support further comprises a wedge which can be inserted between the tray and the pallet for controlling the tilt angle. This feature has a number of advantages: within a certain tilt angle range, any tilt angle can be chosen, whereby the overall tilt angle range may be increased by using a set of wedges with different front angles. The wedge is a simple element which when provided with a low dense interior and a dense surface, is particularly light and low abosrbent and has nonetheless a high form stability.

These and other objects and aspects of the invention will become clear with the following detailed description taken in conjunction with the accompanying drawings.

DETAILED DESCRIPTION OF A PREFERRED EMBODIMENT

Figure 1:
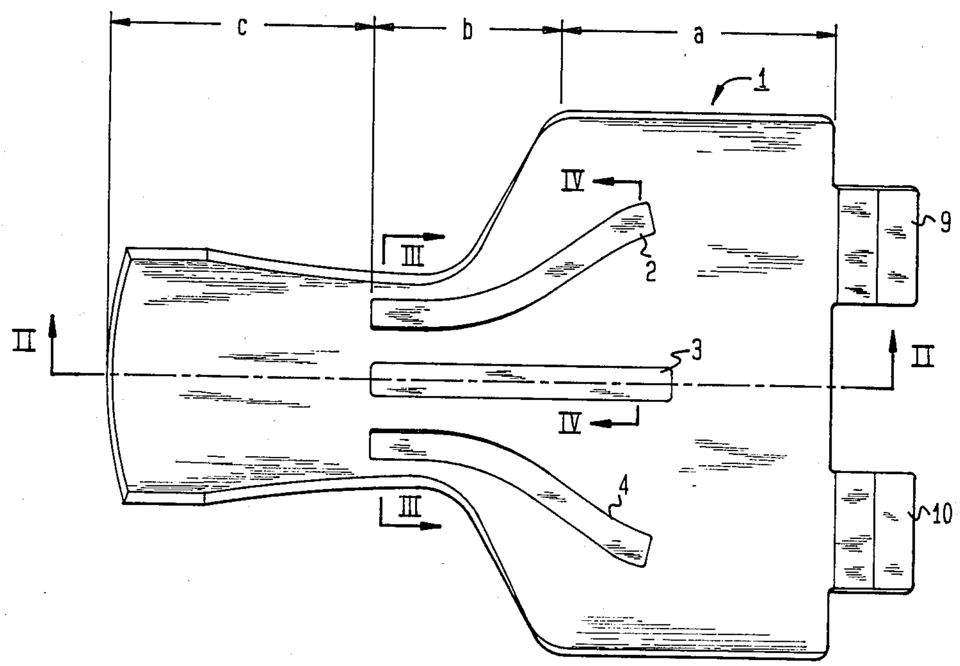
FIG. 1 shows a top view of a tray according to the invention.

In FIG. 1 there is shown a unitary element formed as a tray generally indicated by reference numeral 1. Tray 1 is designed for positioning the upper portion of the patient's body while a gamma camera image is produced. It has a shoulder section, a neck section, and a head section, each section having an axial length a, b and c respectively. All sections are convex (see FIGS. 3-5). They have different radii of curvature to comply with the shape of the supported body parts. The head section has a parabolic profile to prevent major head rotations.

Tray 1 consists advantageously of a polyethylene sheet having a constant wall thickness of 0.25 inches and a weight of less than 1000 g, however, other materials and thickness values may be chosen. The sheet is provided with three indented stiffening sections 2, 3 and 4 extending from about the middle of the shoulder section to nearly the remote end of the neck section. These indentations stiffen the structure—primarily against forces tending to bend the longitudinal axis—so that the thin sheet can carry even very heavy patients. The sheet is however not completely rigid. It yields to a certain extent with respect to transversely extending forces, which change the curvature of the sheet. The support can therefore comply with a variety of morphological features and thus contributes to the patient's comfort and ability to tolerate immobilization for long periods of time. The head section does not require stiffening sections because it is, by virtue of its more pronounced curvature, stiffer by itself. Without additional stiffening means, as in the present embodiment, the head section and its transition to the neck section become so flexible that in case the camera inadvertently bumps the patient's head the risk of injuries is greatly reduced. The support, which in addition has no parts projecting toward the parient, is therefore a very safe aid and allows an extreme juxtaposition of detector and patient required for normally difficult organ imaging.

Figure 2:
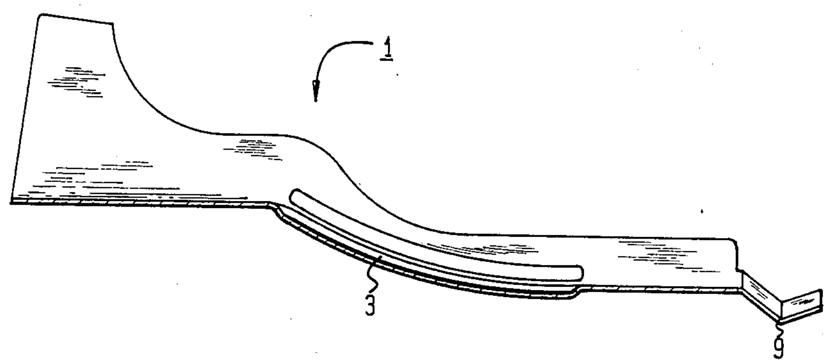
FIG. 2 is a cross-section of the embodiment of FIG. 1, along line II—II.
Figure 3:
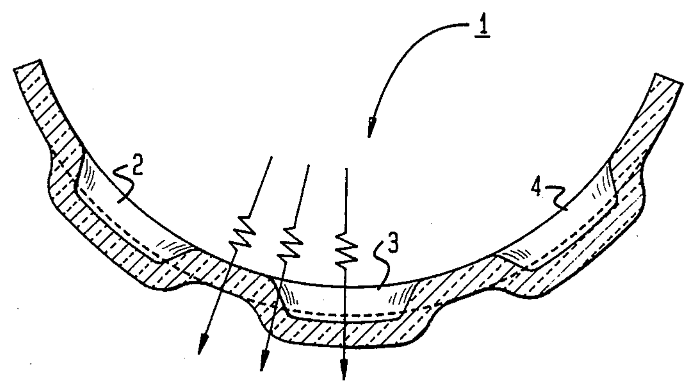
FIG. 3 is a cross-section of the embodiment of FIG. 1, along line III—III.
Figure 4:
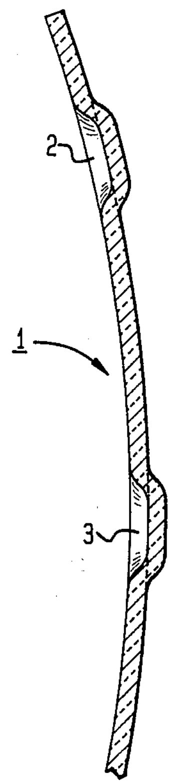
FIG. 4 shows a cross-section of the embodiment of FIG. 1 along line IV—IV, partially broken away.
Figure 5:
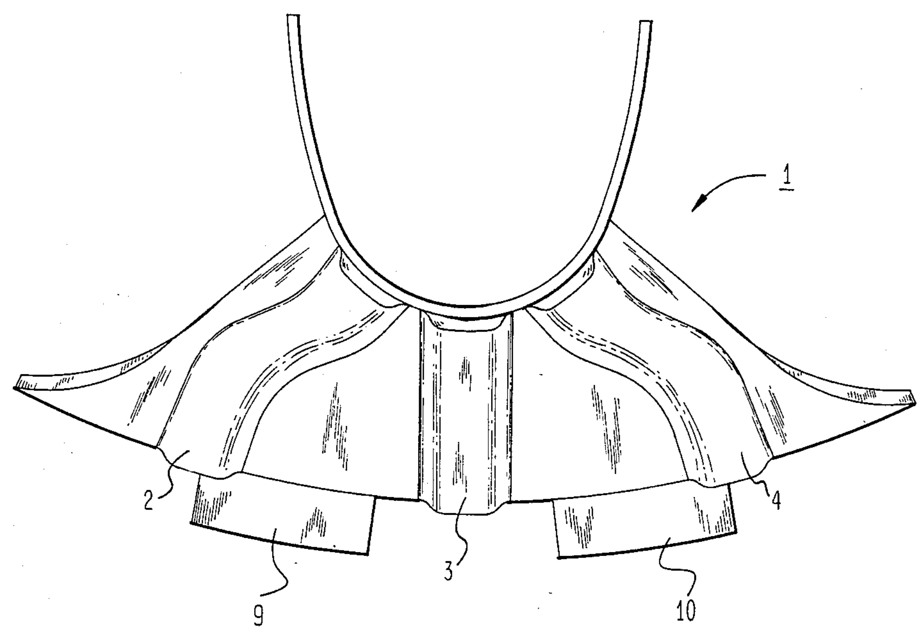
FIG. 5 is a front view of the embodiment of FIG. 1.
Figure 7:
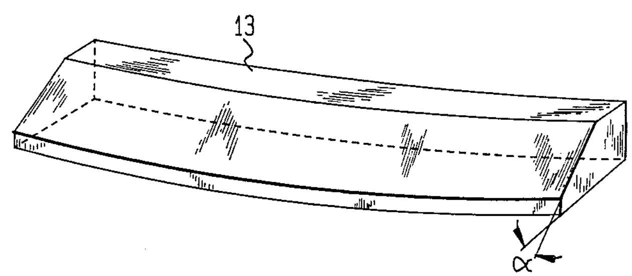
FIG. 7 shows the wedge of FIG. 6 in a perspective view.

The stiffening sections have, as can be seen in FIGS. 2 through 4, in both the longitudinal and cross section, the same type of porfile: a bottom wall parallel to the wall surrounding the indentation and oblique side walls, with rounded transitions between adjacent walls. Because of this profile and the fact that in the stiffening sections the sheet is almost as thick as in its remaining areas, the gamma radiation emitted from a certain area of the patient's body and passing through the sheet on its way to the camera, experiences short travelling distances within a rather limited range. This is illustrated by three representative rays in FIG. 3. Thus, the support is nearly transparent so that a relatively low radiation dose can be applied.

The support is made from polyethylene which has been heated to its softening point and than forced against an open mold by creating a vacuum. This thermoforming technique is known in itself.

Figure 6:
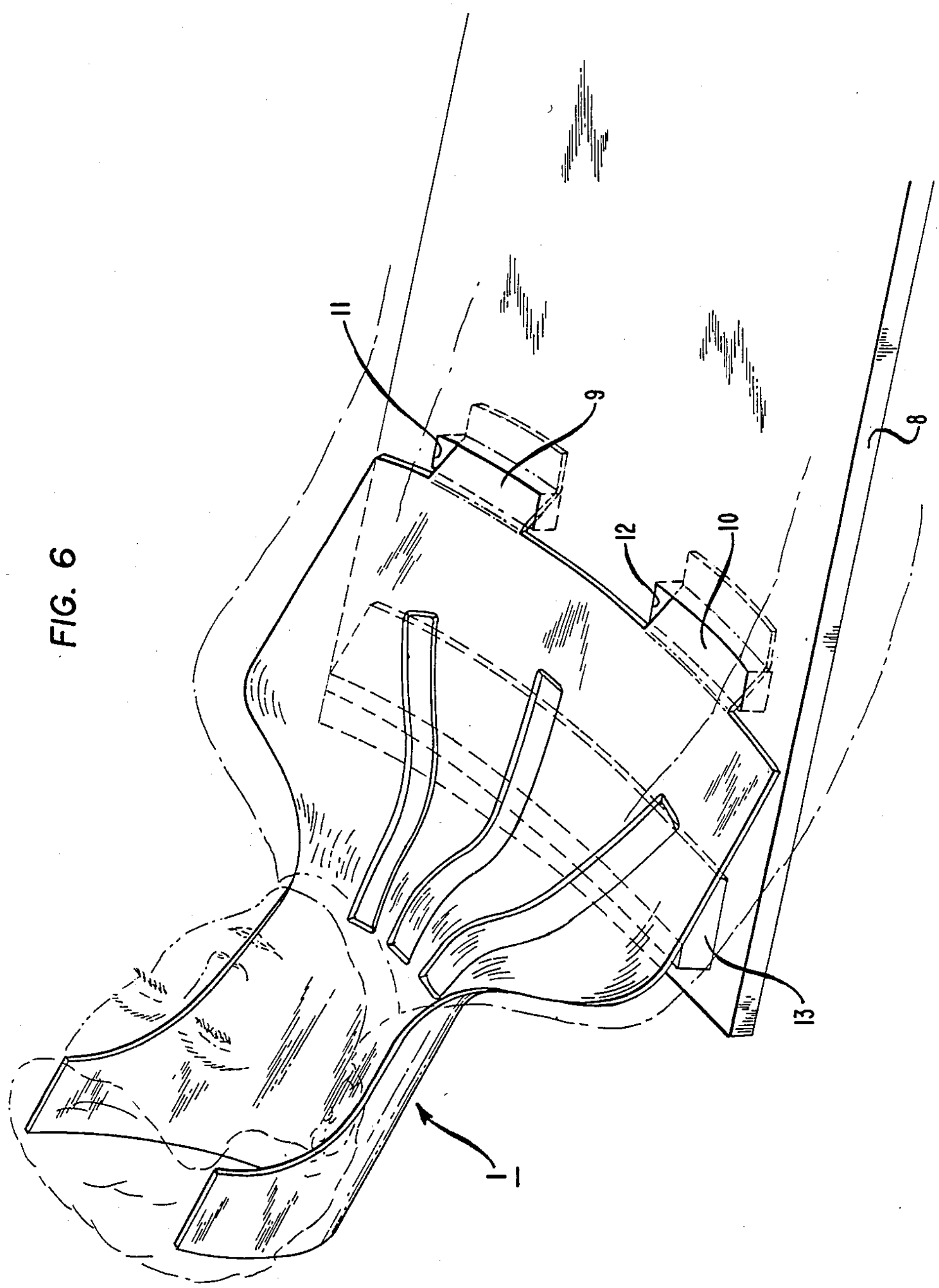
FIG. 6 is a perspective view showing the tray of FIG. 1 interlocked with a pallet and elevated by means of a wedge.

FIG. 6 shows how to attach tray 1 to a patient pallet 8 in a selected tilt position. To this end the shoulder section has at its end remote from the neck section, two offset projecting tabs 9, 10, and the pallet 8 is provided with two holes 11, 12, each hole mating with one of the tabs 9, 10. When the tabs are inserted in the holes, the tray may be tilted around an axis projecting through the pallet holes. The lowest tray position is reached when the tabs strike against the bottom side of the pallet. To elevate the patient's paosition a wedge 13 is inserted between tray 1 and pallet 8. The exact tilt angle is defined by the distance between the tilt axle and the inserted wedge. The total tilt angle range which is required if all facets of the body are to be accessible for the camera, can be covered by three wedges with suitably different front angles $\alpha$.

The wedge consists of a foamed polyurethane molding formed by means of a RIM technique using a metal mold. During injection of the foam mold the surface is kept at a certain temperature which is higher than the temperatures in the mold cavity. With this temperature gradient the molded wedge obtains a low dense core and a dense outer skin, thus being sufficiently rigid, lighter than 300 g and nearly transparent for gamma rays. The RIM technique is also known in itself and therefore need not be described in more detail.

The same wedge structure—less dense bulk and dense surface—may also be obtained by wrapping a suitable tape around a wedge body. This alternative is however more complicated and time consuming.

Having thus described the invention with particular reference to the preferred form thereof, it will be obvious to those skilled in the art to which the invention pertains, after understanding the invention, that various changes and modifications may be made therein without departing from the spirit and scope of the invention as defined by the claims appended hereto.

What is claimed is:

1. A patient support system comprising:

(a) an unitary element of a generally constant wall thickness, said element having shoulder, neck and head sections shaped to receive a patient's shoulders, neck and head respectively, at least two elongated and indented stiffening sections between the shoulder section and the neck section and (b) a pallet for carrying the patient's lower body; and (c) means for tiltably interlocking the element with the pallet.

2. A patient support system according to claim 1, wherein the unitary element consists of a resilient material and the stiffening sections are so dimensioned that the unitary element is capable of carrying the patient's upper body and adapting to different body shapes.

3. A patient support according to claim 2, wherein each stiffening section has a bottom and four sides, the bottom extending parallel to the wall region adjacent the stiffening section and the sides being inclined with respect to the bottom.

4. A patient support according to claim 3, wherein transition sections between neighboring walls are rounded off.

5. A patient support according to claim 2, wherein the element consists of a thermoplastic resin.

6. A patient support according to claim 5, wherein the resin is polyethylene.

7. A patient support according to claim 5, wherein the element has a wall thickness of at most 0.3 inches.

8. A patient support according to claim 2, comprising three stiffening sections extending between the middle of the shoulder section and points adjacent the remote end of the neck section.

9. A patient support according to claim 2, wherein the head section is parabolic in a cross-sectional plane perpendicular to a longitudinal axis of the support.

10. A patient support comprising an unitary element of a generally constant wall thickness, said element having shoulder, neck and head sections shaped to receive a patient's shoulders, neck and head respectively, and having at least two elongated and indented stiffening sections between the shoulder section and the neck section, wherein the shoulder section comprises at least two offset projecting tabs at that end which is remote from the neck section.

11. A patient support system comprising:

(a) an unitary element of a generally constant wall thickness, said element having shoulder, neck and head sections shaped to receive a patient's shoulders, neck and head respectively, at least two elongated and indented stiffening sections between the shoulder section and the neck section and at least two offset projecting tabs at that end of the shoulder section which is remote from the neck section; and (b) a pallet having holes each receiving one of the tabs, whereby the element is tiltably interlocked with the pallet.

12. A patient support system according to claim 11, further comprising a wedge shaped for insertion between the unitary element and the pallet for defining the tilt angle of the element.

13. A patient support system according to claim 11, wherein the wedge consists of a thermosetting resin.

14. A patient support system according to claim 13, wherein the resin is a polyurethane foam.

15. A patient support system according to claim 11, wherein the wedge has a core and an outer skin, said skin being denser than the core.

16. A patient support system according to claim 15, wherein the outer skin is a tape wrapped around the core.

* * * * *